(12) United States Patent
Torun et al.

(10) Patent No.: US 9,645,144 B2
(45) Date of Patent: May 9, 2017

(54) ATOMIC FORCE MICROSCOPE INTEGRATED WITH A MULTIPLE DEGREES-OF-FREEDOM MAGNETIC ACTUATOR

(71) Applicant: Boğaziçi Üniversitesi, Istanbul (TR)

(72) Inventors: Hamdi Torun, Istanbul (TR); Olgac Ergeneman, Zürih (CH); Salvador Pané I Vidal, Zürih (CH); Bradley J. Nelson, Zurih (CH)

(73) Assignee: BOGAZICI ÜNIVERSITESI, Istanbul (TR)

(*) Notice: Subject to any disclaimer, the term of this patent is extended or adjusted under 35 U.S.C. 154(b) by 0 days.

(21) Appl. No.: 15/033,115

(22) PCT Filed: Jul. 31, 2015

(86) PCT No.: PCT/TR2015/050052
§ 371 (c)(1),
(2) Date: Apr. 29, 2016

(87) PCT Pub. No.: WO2016/024931
PCT Pub. Date: Feb. 18, 2016

(65) Prior Publication Data
US 2016/0266107 A1 Sep. 15, 2016

(30) Foreign Application Priority Data
Aug. 15, 2014 (TR) ................. 2014/09565

(51) Int. Cl.
*G01N 33/543* (2006.01)
*G01Q 10/04* (2010.01)
(Continued)

(52) U.S. Cl.
CPC . *G01N 33/54366* (2013.01); *G01N 33/54333* (2013.01); *G01N 33/54346* (2013.01);
(Continued)

(58) Field of Classification Search
CPC ........ G01Q 10/04; G01Q 60/42; G01Q 70/12; G01N 33/54366; G01N 33/54333; G01N 33/54346
See application file for complete search history.

(56) References Cited

U.S. PATENT DOCUMENTS 6,583,411 B1* 6/2003 Altmann ................ B82Y 35/00
250/307
6,690,008 B2* 2/2004 Hantschel .............. B82Y 35/00
73/105

(Continued)

FOREIGN PATENT DOCUMENTS

KR  20130060027 A  6/2013
WO  WO2011029592 A1  3/2011

OTHER PUBLICATIONS

David R Baselt et al "A High-sensitivity Micromachined Biosensor", Proceedings of the IEEE, vol. 85, No. 4, Apr. 1, 1997, pp. 672-680.

(Continued)

Primary Examiner — Shogo Sasaki
(74) Attorney, Agent, or Firm — Gokalp Bayramoglu

(57) ABSTRACT

The present invention relates to a biomolecular measurement system (1), which enables to measure the intermolecular forces arising from the interaction between two biomolecules or the intramolecular forces within a single biomolecule by using an atomic force microscope (AFM). In the present invention, the cantilever (2) is moved only when the actuator (4) moves the magnetic nanowire (3) and thus moves the molecule attached to the end of the magnetic nanowire (3). Since the cantilever (2) is not moved, fluctuation and disturbance is not created in the liquid containing the biomolecules. Thus, the measurements are made more accurately and with higher resolution. Additionally, by means of the actuator (4), the biomolecules are enabled to be (Continued)

moved upon exertion of magnetic force at any coordinate on x, y and z axes on the nanowire (3), or exertion of torque on two axes.

16 Claims, 3 Drawing Sheets

(51) Int. Cl.
  *G01Q 60/42* (2010.01)
  *G01Q 70/12* (2010.01)
(52) U.S. Cl.
  CPC ............ *G01Q 10/04* (2013.01); *G01Q 60/42* (2013.01); *G01Q 70/12* (2013.01)

(56) References Cited

U.S. PATENT DOCUMENTS

| | | | |
|---|---|---|---|
| 7,161,148 B1* | 1/2007 | Givargizov | B82Y 15/00 117/101 |
| 7,357,018 B2* | 4/2008 | Curry | B82Y 15/00 250/307 |
| 8,443,461 B2* | 5/2013 | Ohnesorge | G01Q 40/00 73/105 |
| 8,479,309 B2 | 7/2013 | Yu | |

OTHER PUBLICATIONS

Schemmel A et al. "Single molecule force spectrometer with magnetic force control and inductive detection", Review of Scientific Instruments, AIP, Melville, NY, US, vol. 70, No. 2 Feb. 1, 1999, pp. 1313-1317.

E H. Yang "New fabricatitn method and measurement techniques enable development of nanoscale bimorph actuators" Jun. 23, 2010, SPIE Newsroom, DOI: 10.1117/2.1201006.002602.

Jeong Y et al "Control of tip-to-sample distance in atomic force microscopy: a dual-actuator tip-motion control scheme", Review of Science Instruments., Sep. 2007;78(9):093706.

A Fakhraee et al "Electromagnetically Actuated Cantilevers Using Magnetic Micropillars for Atomic Force Microscopy", IEEE International Magnetics Conference, May 4-8, 2014, Dresden, Germany.

* cited by examiner

ATOMIC FORCE MICROSCOPE INTEGRATED WITH A MULTIPLE DEGREES-OF-FREEDOM MAGNETIC ACTUATOR

FIELD OF THE INVENTION

The present invention relates to an atomic force microscope integrated with a multiple degrees-of-freedom magnetic actuator which enables to measure interaction forces between two molecules or intramolecular forces within a single molecule, and a measurement system using magnetic nanowires and other nano structures.

BACKGROUND OF THE INVENTION

Atomic force microscopy (AFM) has become an important tool in nanoscale science and applications. A microsized passive cantilever structure in a general AFM arrangement is used to measure interaction forces between a sharp needle integrated with the cantilever and a surface that the needle interacts with. The cantilever is moved over the surface by the help of a piezo actuator. In the meantime, the force acting on the cantilever causes bending on the cantilever depending on its spring constant. Bending is measured by optical means. FIG. 1 conceptually shows an AFM cantilever scanning the surface, the closed-loop control system that controls operation thereof and detection optics.

AFM is the most commonly used technology for single-molecule mechanics measurements thanks to its versatility. Commercially available AFM cantilevers provide force resolution of few picoNewtons (pN) in liquid. Cantilevers should be actuated within a specific speed range for AFM-based dynamic force spectroscopy applications. Higher dynamic range for actuation and detection is required along with higher force resolution for improved dynamic force spectroscopy. The pulling speed of the cantilever by using a piezo actuator determines the molecular loading rate in a conventional AFM system.

Hydrodynamic drag force on the moving cantilever increases with the pulling speed. Drag force may reach the level of biomolecular forces, which is desired to be measured, even at moderate speed levels, i.e., a few tens of µm/s for most of the cantilevers in use. However higher pulling speed capability is required for complete understanding of energy landscapes. In the light of these, the need for novel force sensors and technologies that allow high loading rates with minimal hydrodynamic drag forces on the force sensors can be put in a proper context.

Magnetic micro-beads are frequently used for actuating biomolecules by magnetic particles. The present invention, which enables manipulation of biomolecules for investigating their conformational behavior with high precision along multiple degrees of freedom, is fundamentally different from the approaches used in conventional magnetic manipulation systems in which magnetic beads are used. The magnetic micro-beads are typically made of iron oxide particles covered by polymer matrices. A spherical single domain magnetite particle with a diameter of 100 nm cannot exert forces in excess of tens of picoNewtons given practical limitations on the generation of magnetic field gradients, and is incapable of generating torque due to its geometry. This is a significant limitation in their use. The size of the particles may be increased to increase the attainable force levels; however, surface area of magnetic particles with diameters larger than 1 µm is much larger than an area to which a single biomolecule can bind. Therefore, their use in single-molecule measurements is limited. High aspect ratio magnetic nanowires address this bottleneck. Magnetic nanowires exhibit larger magnetic moments as compared to the beads because of their higher volume and their inherent magnetic shape anisotropy. Upon comparing the attainable force levels, it was observed that nickel magnetic nanowires outperformed magnetic beads of the same volume by a factor of two. Moreover, when increasing the volume of nanowires, the size of its tip binding to the molecules does not have to be increased. Volume of a nanowire can be increased by extending its length while keeping its diameter small enough so that it can still interact with single molecules. Additionally, nanowires can also generate torque thanks to their geometric forms.

The International patent application document no. WO2011029592, an application in the state of the art, discloses a magnetic manipulation device for magnetic elements.

The structure disclosed in U.S. Pat. document No. U.S. Pat. No. 8,479,309B2, an application in the state of the art, is a novel AFM cantilever. An improved measurement cantilever is produced by means of a nano-needle integrated to an AFM cantilever and it is disclosed that by means of this cantilever improvements are achieved in the measurements conducted in liquid. This method is aimed for developing a new cantilever, and the nano-needle arranged on the cantilever only provides a new geometry to the cantilever. The innovation disclosed by the biomolecular measurement system of the present invention is combination of magnetic nanowires with biomolecules and using the nanowires as actuators. In the bimolecular measurement system of the present invention, the nanowires are integral part of the measurement system and they provide magnetic actuation capability.

The document titled "New fabrication methods and measurement techniques enable development of nanoscale bimorph actuators" (E. H. Yang, 23 Jun. 2010, SPIE Newsroom. DOI: 10.1117/2 1201006.002602) presents nano-scale actuators produced with bimorph structures. The feature of bimorph structures is that they bend under temperature difference. By means of this feature, it is possible to exert force at micro and nano-scale. The nano-structures are used to exert force on biological structures. The nanowires used in the biomolecular measurement system of the present invention are the actuators of the AFM system. The nanowires described in the present invention are magnetic actuators and differ from the nano-structures of bimorph actuators in terms of both function and structure.

The article titled "Control of tip-to-sample distance in atomic force microscopy: a dual-actuator tip-motion control scheme" (Jeong Y, Jayanth G R, Menq C H., Rev Sci Instrum. 2007 September; 78(9):093706) describes actuation of a standard AFM cantilever by a magnetic particle adhered on the AFM cantilever. The mechanical structure moved in this system is the cantilever itself and the magnetic particle is fixed to the cantilever. In the biomolecular measurement system of the present invention, the moving structure is nanowire whereas the cantilever is fixed. The cantilever moves only as a result of biomolecular interaction forces. It does not move due to the signal applied to the actuator. Thus, low noise and high stability measurements can be performed.

The document titled "Electromagnetically Actuated Cantilevers Using Magnetic Micropillars for Atomic Force Microscopy" (A Fakhraee, N Shamsudhin, S Sevim, A Lindo, S Pane, O Ergeneman, H Torun, B Nelson, IEEE International Magnetics Conference, May 4-8 2014, Dresden, Germany) discloses that the cantilever is moved by the magnetic forces in an application similar to the structure described by the document titled "Control of tip-to-sample distance in atomic force microscopy: a dual-actuator tip-motion control scheme". A micropillar is adhered onto the cantilever. The actuation method formed by an electromagnet is different from the method used in the biomolecular measurement system of the present invention. In the present invention, while the cantilever remains fixed, the magnetic nanowires are actuated by the actuator signal. Furthermore, the nanowires in the present invention are much smaller than the micropillars described in the mentioned document.

SUMMARY OF THE INVENTION

Usually piezotube actuators are used in AFM systems as actuators. The approach in the present invention is use of a nanostructure actuator miniaturized down to the size of a single macromolecule as an actuator for biomolecular measurements. The innovative actuation method proposed here will advance beyond the state of the art in the field of single-molecule studies. The implementation of the actuator will be based on a five degrees-of-freedom (three translational and two rotational) wireless magnetic manipulator. At the heart of the magnetic manipulator, there lies a magnetic nanowire or a magnetic micro/nano-structure. Thus the footprint of the actuator will be orders of magnitude smaller than the commonly used piezotubes. Use of miniaturized mechanical actuator improves system dynamics. It enhances resolution and stability of the system. Drift and system complexity due to a larger scale piezo actuator can be eliminated.

An unprecedented improvement can be provided over the system dynamics by using magnetic nanowires as actuators and keeping the cantilevers fixed. In this architecture, an AFM cantilever is attached to a macromolecule that is already attached to a magnetic nanowire. Under the externally controlled magnetic fields and field gradients, it is possible to manipulate the molecule along multiple degrees-of-freedom without a substrate surface. Manipulation tasks with objects varying in dimensions from nanometers to centimeters with five degrees-of-freedom with high resolution that is limited by imaging technology have already been demonstrated with electromagnetic manipulation setups. Electromagnetic coils, magnets or both can be used at the same time in varying arrangements for the magnetic manipulation of objects. Using nanowires made of soft magnetic materials (e.g., Permalloy, Nickel, iron, Cobalt or alloys comprising these materials), manipulation is accomplished using relatively small magnetic fields (a few hundreds Oe).

On the nanometer scale, manipulation of different types of structures such as nanocoils, nanowires and nanotubes with different motion strategies such as gradient based translational motion and field based rotational motion have been demonstrated. Use of magnetic nanowires offers various advantages over other magnetic nanostructures. They exhibit strong geometric anisotropy due to their high aspect ratio. Therefore, in addition to linear pulling, it is possible to apply torque on the nanowires under the influence of rotating magnetic field. Complete energy landscape of the molecules can be obtained thanks to the new actuation method. Also, molecular unfolding/folding/refolding mechanisms can be investigated With an unprecedented detail and accuracy using magnetic nano-actuators. An immediate application will be elucidating folding/unfolding pathways of single protein molecules. A magnetic nanowire encounters drastically smaller hydrodynamic drag forces in viscous fluids as compared to larger structures. The drag (hence damping) on a mechanical system is an indication of thermal noise according to the fluctuation dissipation theorem. Reduced hydrodynamic drag improves force resolution significantly.

Thus, the most important objective of the present invention is to utilize a low noise AFM system. The proposed method is unique in its ability to detect the slightest conformational changes on a single molecule level in contrast to the current technologies. This system promises a leap forward in characterizing proteins and probing, their structure and function.

The proposed biomolecular measurement system is capable of probing biomolecular interactions:
under controlled forces and excitations with multiple degrees-of-freedom,
at a much higher dynamic rate to elucidate the complete energy landscape of single molecular interactions, and
at physiological rates (i.e. long time scale biophysical experiments) by reducing drift and increasing stability.

In this architecture of this biomolecular measurement system
magnetic nanowires are functionalized with biomolecules.
AFM cantilever picks biomolecules that are already anchored to nanowires.
magnetic nanowires are actuated using one or more electromagnets or magnets that apply force and torque in multiple degrees-of-freedom,
the interaction forces within the biomolecules or between the different types of biomolecules attached to nanowires are detected using the AFM cantilever.

A novel and improved single molecule measurement system is proposed by combining AFM technology with magnetic positioning by means of the present invention. Inter/intra-molecular interactions of biomolecules are investigated with high precision along multiple degrees-of-freedom at single molecule level with the new technology. This objective is supported by integration of the electromagnetic nano-actuators with the molecules. By means of reduction of the size of the actuators to the size of molecules, molecule positioning at multiple degrees-of-freedom and detection at single-molecule level are possible. High stability experiments can be conducted by means of the newly developed biomolecular measurement system. Furthermore, speed and manipulation capabilities of the novel actuators will enable improved AFM experiments. By means of the positioner that will be formed by nanowires, molecules attached between the nanowire and the lever can be pulled in different directions and torque can be applied under rotating magnetic field and angular positioning can be performed. For this reason, molecular folding/unfolding/refolding mechanisms can be completely elucidated by the actuators produced with the mentioned structures.

BRIEF DESCRIPTION OF THE DRAWINGS

Biomolecular measurement system developed to fulfill the objective of the present invention is illustrated in the accompanying figures, in which.

Figure 1:
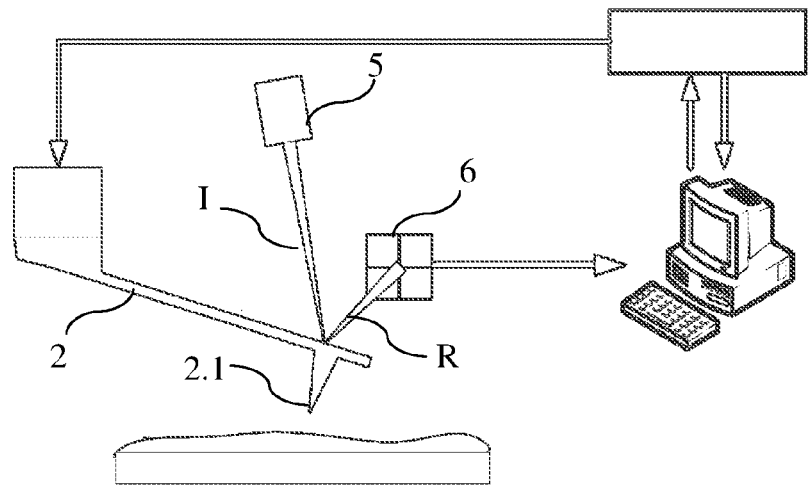
FIG. 1 is a view of the atomic farce microscope used in the prior art.
Figure 2:
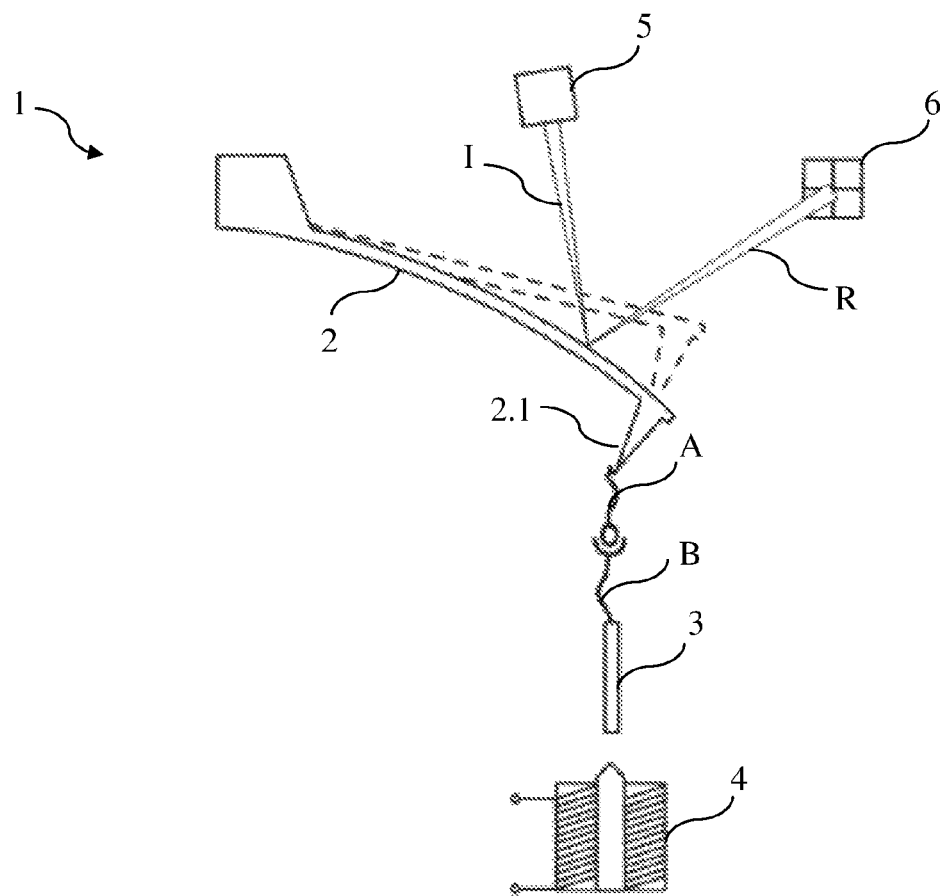
FIG. 2 is a view of the biomolecular measurement system that enables measurement of interaction forces between two molecules.

The components in the figures are given reference numbers as follows:
7. Biomolecular measurement system
8. Cantilever
9. Magnetic nanowire
10. Actuator
11. Laser source
12. Photodetector
R. Reflected light
I. Incoming light
A. Molecule A
B. Molecule B

DETAILED DESCRIPTION OF THE INVENTION

A biomolecular measurement system (1), which enables to measure the intermolecular forces arising from the interaction between two biomolecules or the intramolecular forces of a single biomolecule by using an atomic force microscope (AFM), basically comprises
at least one cantilever (2) which remains fixed and changes position only upon movement of the molecules without using any actuator,
at least one cantilever tip (2.1) having a diameter that allows binding of a single biomolecule,
at least one magnetic nanowire (3), to the end of which a single molecule can bind, and which enables to move the molecules,
at least one actuator (4) which, by applying magnetic field to the magnetic nanowire (3), enables to pull and push the magnetic nanowire (3) at any coordinate on x, y, z axes and to apply torque on the magnetic nanowire (3) in two different axes,
at least one laser source (5) which projects light on the cantilever (2),
at least one photodetector (6) on which the light (R) reflected from the cantilever (2) is projected.

The cantilever (2) provided in the biomolecular measurement system (1) of the present invention is fixed and is not moved by any actuator. The cantilever (2) has a pointed cantilever tip (2.1) having a diameter that allows binding of only a single biomolecule. The cantilever tip (2.1) can be a tip produced from materials, such as gold, silicon, silicon nitride or silicon oxide that allow attachment of the biomolecules.

Figure 3:
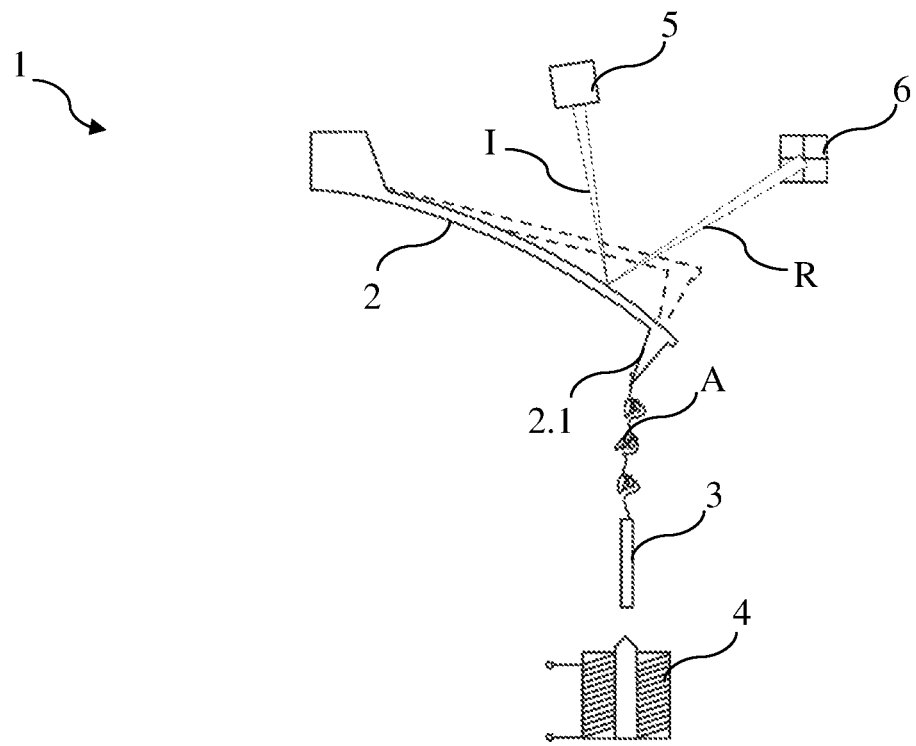
FIG. 3 is a view of the biomolecular measurement system that enables unfolding and folding of a single molecule.
Figure 4:
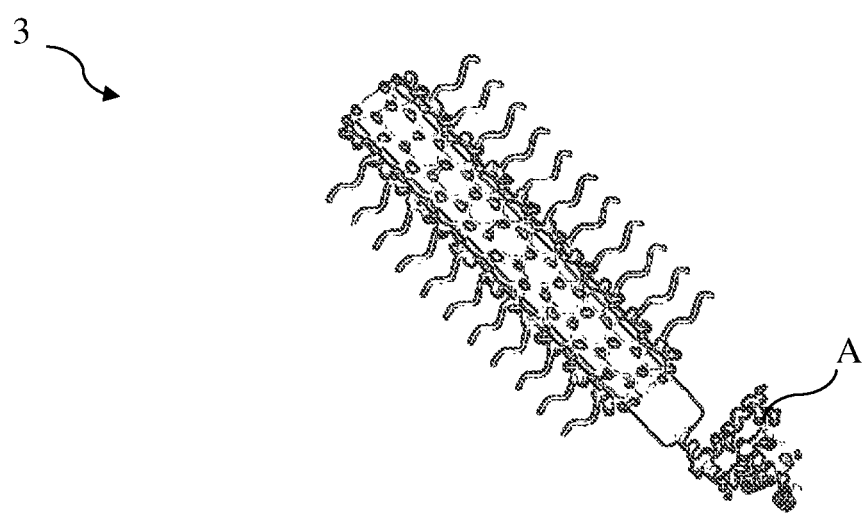
FIG. 4 is a perspective view of the nanowire.
Figure 5:
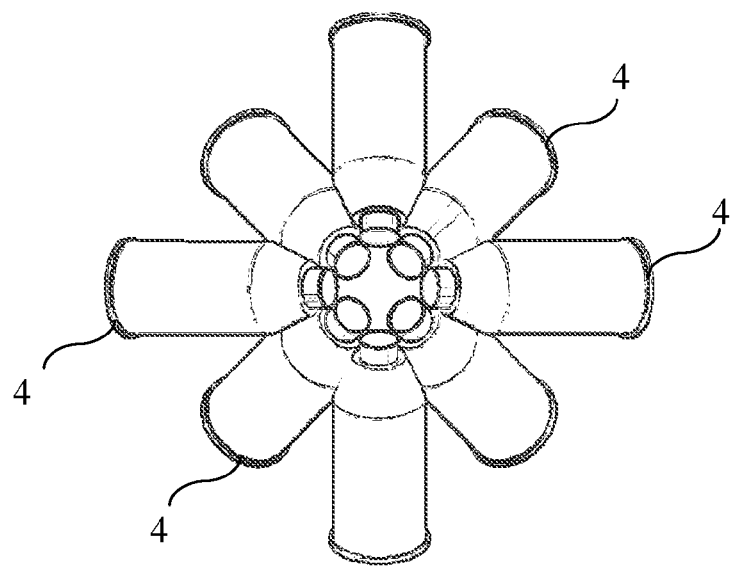
FIG. 5 is a view of a manipulator formed by multiple electromagnets.

In a preferred embodiment of the invention, in order to measure the forces between two biomolecules (for example molecule A and molecule B), one of the biomolecules is attached to the cantilever tip (2.1) while the other biomolecule binds to the end of the magnetic nanowire (3). The magnetic nanowire (3) is a cylindrical structure preferably having a length of 1 μm (micrometer) and a diameter of 100 nm (nanometer). The end of the said magnetic nanowire (3), which is the area of attachment for the biomolecules, is made of gold or polymer, while the other parts can be made of a magnetic material, which does not bind to the molecules, preferably cobalt, iron, nickel or an alloy comprising at least one of these metals. Thus the magnetic nanowire (3) acts as a magnet and can be pushed and pulled by the actuator (4) by applying a magnetic field. An example magnetic nanowire (3) is shown in FIG. 3.

In order to measure the interaction force between the biomolecules binding to the cantilever tip (2.1) and the magnetic nanowire (3) end, these biomolecules should be actuated. An actuator (4) positioned at the lower part of the magnetic nanowire (3) is used for this purpose. This actuator (4) may comprise at least one electromagnet magnet, Helmhotz coil or at least one of these structures. The said actuator (4) is driven by a driver electronics (not shown in the figures), magnetic force is applied to the magnetic nanowire (3) by passing current through the cables wound around the core of the electromagnet, and thus the biomolecules attached between the cantilever tip (2.1) and the magnetic nanowire (3) are moved. Due to the movement of the biomolecules actuated by the actuator (4), the cantilever tip (2.1) and thus the cantilever (2) move at any coordinate on the x, y and z axes in the direction of the biomolecules or make a rotational movement.

A laser source (5) and a photodetector (6) located at the upper part of the cantilever (2) are used to measure the interaction between the biomolecules. A split photodetector can be used as a photodetector (6), for detection of the movement of the cantilever at linear axes and a quadrature photodetector can be used for detection of the torque movement. The incoming light (1) coming from the laser source (5) onto the reflector surface of the cantilever (2) is projected on the photodetector (6) right in the center. The angle of the cantilever with respect to its neutral axis (2) changes due to the movement of the biomolecules and the light reflected from the cantilever (2) is projected not in the center but at a different region of the photodetector (6).

Figure 6:
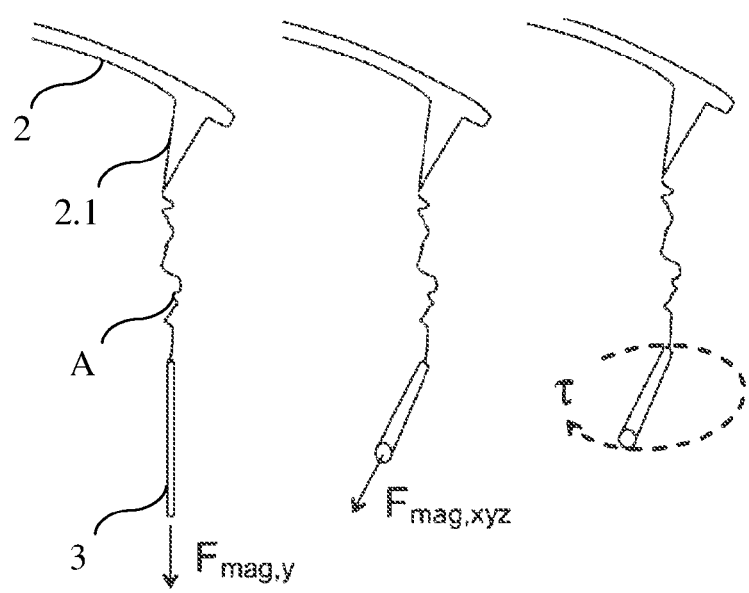
FIG. 6 is a representative view of the forces applied to the magnetic nanowire—in order to actuate a magnetic nanowire—at y axis and xyz axis respectively and the torque applied to the magnetic nanowire.

The molecules can be moved at any coordinate on x, y, z axes by using the magnetic nanowires (3). FIG. 6 (left) shows how the magnetic nanowire (3) is pulled downwards by means of the force exerted by the actuator (4) onto the nanowire (3) on y axis. FIG. 6 (middle) shows the force exerted by the actuator (4) onto the magnetic nanowire (3) at any coordinate on x, y and z axes. The force on the magnetic nanowire (3) can be increased by extending the length of the magnetic nanowire (3).

Thanks to use of magnetic nanowires (3) instead of magnetic spheres, in addition to the force in at least one preferably three different axes, torque in least one preferably three different axes can also be applied by the actuator (4) on the magnetic nanowire (3). FIG. 6 (right) shows the torque applied to the magnetic nanowire (3). Applying torque on the magnetic nanowire (3) enables for example double helix DNAs to recoil. By means of an actuator (4) functioning as a positioner that will be formed by electromagnets, the molecules attached between the magnetic nanowire (3) and the cantilever tip (2.1) can be pulled in different directions and torque can be applied under rotating magnetic field and angular positioning can be performed. To this end, the magnetic nanowire (3) can be positioned precisely in a spherical working field by means of an actuator (4) that will be formed by bringing eight electromagnets together. For this reason, molecular folding/unfolding/refolding mechanisms can be completely performed by the actuators (4) formed with the said electromagnets.

In another embodiment of the invention, instead of measuring the interactions between two biomolecules, it is enabled to elucidate unfolding/folding pathways and dynamics of a single biomolecule such as a protein. For example, proteins unfold like a string when they take part in enzymatic interaction, and then when they are done, they refold. Some critical diseases occur when the proteins, after unfolding and fulfilling their function, get misfolded. For example, Alzheimer is one of these diseases. If a typical protein in the brain is unfolded, carries out its function and then folds incorrectly, it cannot unfold again. Examination of this is very important in single molecule level.

In order to examine the intramolecular forces of a single biomolecule, one end of the said biomolecule is attached to the magnetic nanowire (3) while the other end thereof is attached to the cantilever tip (2.1). As in the previous application, the magnetic nanowire (3) is subjected to the magnetic field formed by passing current through the coils of electromagnets (4) and the magnetic nanowire (3) is moved forward and backward. Thus the biomolecule at the end of the magnetic nanowire (3) is enabled to be unfolded and folded. The biomolecule moves the cantilever tip (2.1) when being unfolded and folded, and this movement enables the light projected by the laser (5) on the reflector surface of the cantilever (2) to be reflected at a different angle and to be projected to a position which is different from the position where the reflected light (R) is first projected on the photodetector. Pathways and dynamics of unfolding and folding of the biomolecule can be elucidated also by calculation of the difference of position of the light projected on the photodetector (6).

In the biomolecular measurement system (1) of the present invention, thanks to not using an actuator to move the cantilever (2), a fluctuation is not created in the liquid in which the biomolecules are present. This in turn prevents the measurements from getting adversely affected.

The invention claimed is:

1. A biomolecular measurement apparatus, which enables to measure the intermolecular forces arising from the interaction between two biomolecules or the intramolecular forces of a single biomolecule by using an atomic force microscope, comprising:
   at least one cantilever which remains fixed;
   at least one cantilever tip to which the single biomolecule can bind;
   at least one magnetic nanowire to the end of which the single biomolecule can bind;
   the single molecule which can hind to the end of the magnetic nanowire can bind to an other biomolecule which can bind to the cantilever tip or to
   the cantilever tip
   so that the two biomolecules bound together or the single biomolecule can be located between the magnetic nanowire and the cantilever tip, wherein the cantilever tip is pointed and has a radius of curvature at an apex of the cantilever tip that allows binding of only a single biomolecule;
   at least one laser source which projects light on the cantilever;
   at least one photodetector on which the light reflected from the cantilever is projected;
   at least one actuator which, by applying magnetic force to the magnetic nanowire, enables to pull and push the magnetic nanowire on x, y, z axes, wherein,
   the magnetic nanowire moves by means of the magnetic force exerted by the actuator and enables to move the single biomolecule or the two biomolecules attached to the end of the magnetic nanowire; and
   the cantilever makes a movement at any coordinate on the x, y and z axes in the direction of the single biomolecule or the two biomolecules without using any actuator, only by means of the movement of the single biomolecule or the two biomolecules actuated by the actuator,
   wherein the end of the magnetic nanowire that is the area of attachment for the single biomolecule or one of the two biomolecules is produced from gold or polymer, and other parts of the magnetic nanowire are made of a magnetic material which does not bind to the single biomolecule.

2. The biomolecular measurement apparatus of claim 1, wherein the cantilever tip is produced from materials that allow attachment of the single biomolecule or the two biomolecules, which is selected from the group consisting of gold, silicon, silicon nitride or silicon oxide.

3. The biomolecular measurement apparatus of claim 1, wherein the other parts of the magnetic nanowire are made of an item selected from the group consisting of cobalt, iron, nickel or an alloy comprising at least one of these metals.

4. The biomolecular measurement apparatus of claim 1, wherein at least one actuator comprises at least one electromagnet, magnet, Helmhotz coil or at least one of these structures.

5. The bimolecular measurement apparatus of claim 1, wherein the actuator, in order to measure the interaction force between the two biomolecules, one of which is attached to the cantilever tip and the other to the magnetic nanowire, applies magnetic field to the magnetic nanowire and thereby enables the two biomolecules attached to the magnetic nanowire to be moved.

6. The biomolecular measurement apparatus of claim 1, wherein the actuator enables to apply force in at least one preferably three different axes on the magnetic nanowire.

7. The biomolecular measurement apparatus of claim 1, wherein the actuator, by means of a positioner that will be formed by using a plurality of electromagnets, enables the single biomolecule or the two biomolecules attached between the magnetic nanowire and the cantilever tip to be pulled in different directions under magnetic field.

8. The biomolecular measurement apparatus of claim 1, wherein the actuator, in order to measure the intramolecular force of the single biomolecule, one end of the single biomolecule is attached to the cantilever tip and an other end of the single biomolecule is attached to the magnetic nanowire; applies magnetic field to the magnetic nanowire and thereby enables the single biomolecule to unfold or fold.

9. The bimolecular measurement apparatus of claim 1, wherein the movement of the cantilever is a rotational movement.

10. The bimolecular measurement apparatus of claim 9, wherein the cantilever tip is produced from materials that allow attachment of the biomolecules, which is selected from the group consisting of gold, silicon, silicon nitride or silicon oxide.

11. The biomolecular measurement apparatus of claim 9, wherein the other parts of the magnetic nanowire are made of an item selected from the group consisting of cobalt, iron, nickel or an alloy comprising at least one of these metals.

12. The biomolecular measurement apparatus of claim 9, wherein at least one actuator comprises art least one electromagnet, magnet, Helmhotz coil or at least one of these structures.

13. The biomolecular measurement apparatus of claim 9, wherein the actuator, in order to measure the interaction force between the two biomolecules, one of which is attached to the cantilever tip and the other to the magnetic nanowire, applies magnetic field to the magnetic nanowire and thereby enables the two biomolecules attached to the magnetic nanowire to be moved.

14. The biomolecular measurement apparatus of claim 9, wherein the actuator enables to apply torque in least one preferably three different axes on the magnetic nanowire.

15. The biomolecular measurement apparatus of claim 9, wherein the actuator, by means of a positioner that will be formed by using a plurality of electromagnets, enables the single biomolecule or the two biomolecules attached between the magnetic nanowire and the cantilever tip to be pulled in different directions and torque to be applied under rotating magnetic field and angular positioning to be performed.

16. The biomolecular measurement apparatus of claim 9, wherein the actuator, in order to measure the intramolecular force of the single biomolecule, one end of the single biomolecule is attached to the cantilever tip and the other end of the single biomolecule is attached to the magnetic nanowire; applies magnetic field to the magnetic nanowire and thereby enables the single molecule to unfold or fold.

\* \* \* \* \*